United States Patent [19]

McGary et al.

[11] Patent Number: 5,053,010
[45] Date of Patent: Oct. 1, 1991

[54] SAFETY SYRINGE WITH RETRACTABLE NEEDLE

[75] Inventors: R. Kern McGary; S. William Jentzen, both of Cedar Creek, Tex.

[73] Assignee: Triad Technology, Austin, Tex.

[21] Appl. No.: 592,504

[22] Filed: Oct. 3, 1990

[51] Int. Cl.⁵ .............................................. A61M 5/00
[52] U.S. Cl. ..................................... 604/110; 604/195
[58] Field of Search ............... 604/195, 110, 187, 263, 604/198

[56] References Cited

U.S. PATENT DOCUMENTS

| | | |
|---|---|---|
| 4,650,468 | 3/1987 | Jennings, Jr. . |
| 4,675,005 | 6/1987 | DeLuccia . |
| 4,767,413 | 8/1988 | Haber et al. . |
| 4,781,692 | 11/1988 | Jagger et al. . |
| 4,790,822 | 12/1988 | Haining . |
| 4,790,827 | 12/1988 | Haber et al. . |
| 4,790,828 | 12/1988 | Dombrowski et al. . |
| 4,801,295 | 1/1989 | Spencer . |
| 4,804,370 | 2/1989 | Haber et al. . |
| 4,804,371 | 2/1989 | Vaillancourt . |
| 4,804,372 | 2/1989 | Laico et al. . |
| 4,813,936 | 3/1989 | Schroeder . |
| 4,826,483 | 5/1989 | Molnar . |
| 4,826,484 | 5/1989 | Haber et al. . |
| 4,826,488 | 5/1989 | Nelson et al. . |
| 4,826,489 | 5/1989 | Haber et al. . |
| 4,826,490 | 5/1989 | Byrne et al. . |
| 4,826,491 | 5/1989 | Schramm . |
| 4,838,869 | 6/1989 | Allard ................................ 604/195 |
| 4,850,977 | 7/1989 | Bayless . |
| 4,861,338 | 8/1989 | Mathiesen et al. . |
| 4,863,435 | 9/1989 | Sturman et al. . |
| 4,874,382 | 10/1989 | Lindemann et al. . |
| 4,894,055 | 1/1990 | Sudnak . |
| 4,900,307 | 2/1990 | Kulli . |
| 4,908,022 | 3/1990 | Haber . |
| 4,917,679 | 4/1990 | Kronner . |
| 4,921,486 | 5/1990 | DeChellis et al. . |
| 4,927,414 | 5/1990 | Kulli . |
| 4,946,446 | 8/1990 | Vadher . |
| 4,955,870 | 9/1990 | Ridderheim et al. ............... 604/195 |
| 4,994,034 | 2/1991 | Botich et al. ......................... 604/110 |

OTHER PUBLICATIONS

Official Gazette, Aug. 29, 1989, pp. 3210-3211.
Official Gazette, May 2, 1989, pp. 355-356.
Official Gazette, May 2, 1989, pp. 357-358.
Official Gazette, Mar. 21, 1989, pp. 1591-1592.
Official Gazette, Feb. 14, 1989, pp. 754-755.
Official Gazette, Jan. 31, 1989, p. 2356.
Official Gazette, Dec. 13, 1988, pp. 752-753.
Official Gazette, Nov. 1, 1988, pp. 281, 284.
Official Gazette, Dec. 13, 1988, p. 754.
Official Gazette, Jun. 23, 1987.
Official Gazette, Feb. 13, 1990, p. 855.

*Primary Examiner*—John D. Yasko
*Attorney, Agent, or Firm*—Arnold, White & Durkee

[57] ABSTRACT

An improved safety syringe with retractable needle is provided which allows retraction of the needle into a hollow plunger by additional forward pressure on the plunger after the fluid is driven from the syringe. The present invention contemplates an improved syringe device with retractable needle, and a method of delivering fluid to a patient and retracting the needle within the syringe after the fluid is delivered. The syringe preferably includes a hollow plunger inserted into one end of a cylindrical barrel and a hollow needle attached to the other end of the barrel. Biasing means is attached to the barrel for biasing the needle toward the hollow plunger, and means is provided for releasing the needle into the hollow plunger by applying additional forward pressure upon the plunger after the plunger is fully extended into the barrel. The present invention is particularly convenient for the operator to use in a one-handed fashion and is relatively uncomplicated and easy to manufacture. Further, the present invention is non-reusable after the needle is retracted thereby preventing reuse of a potentially contaminated syringe.

31 Claims, 6 Drawing Sheets

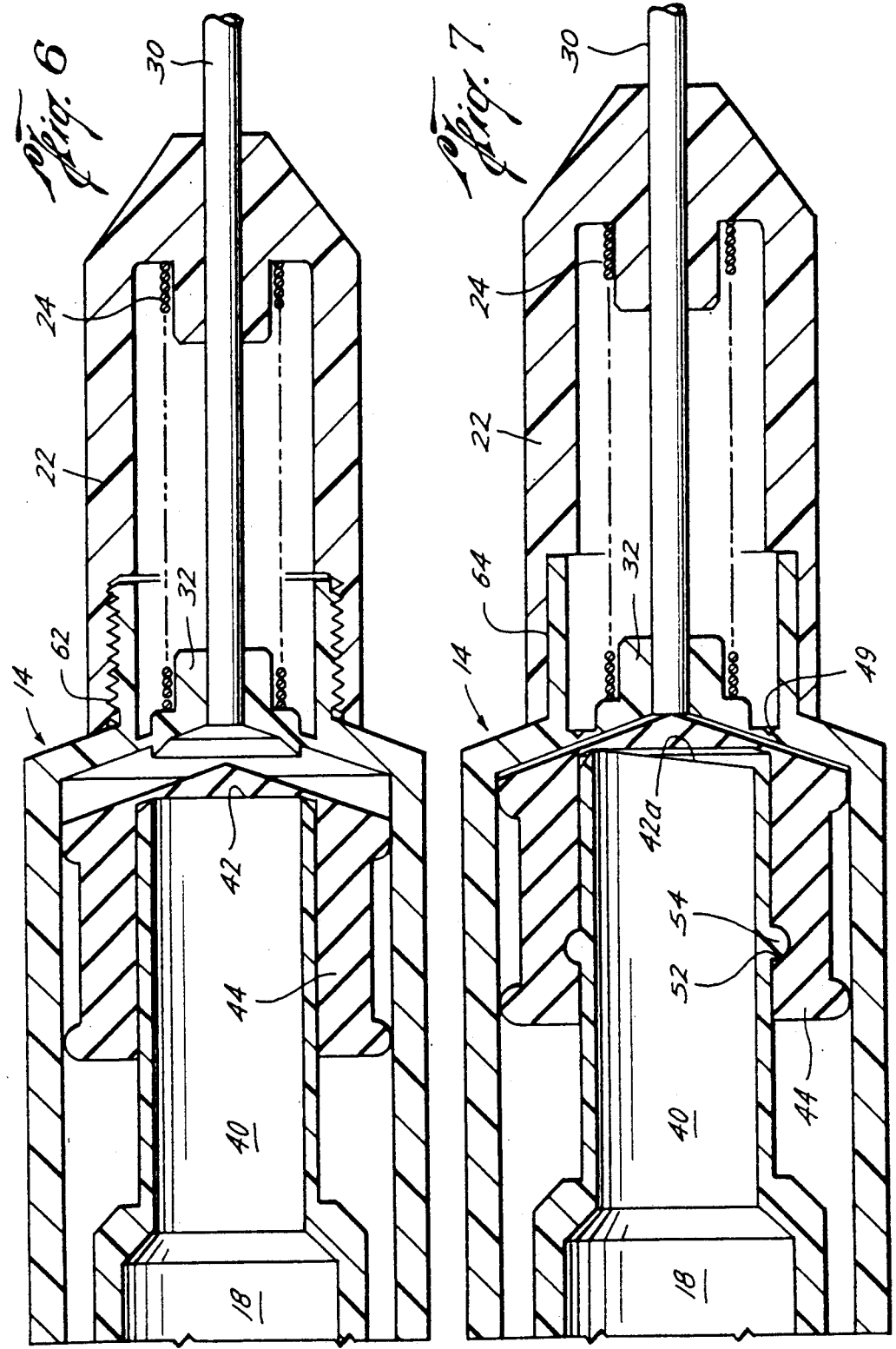

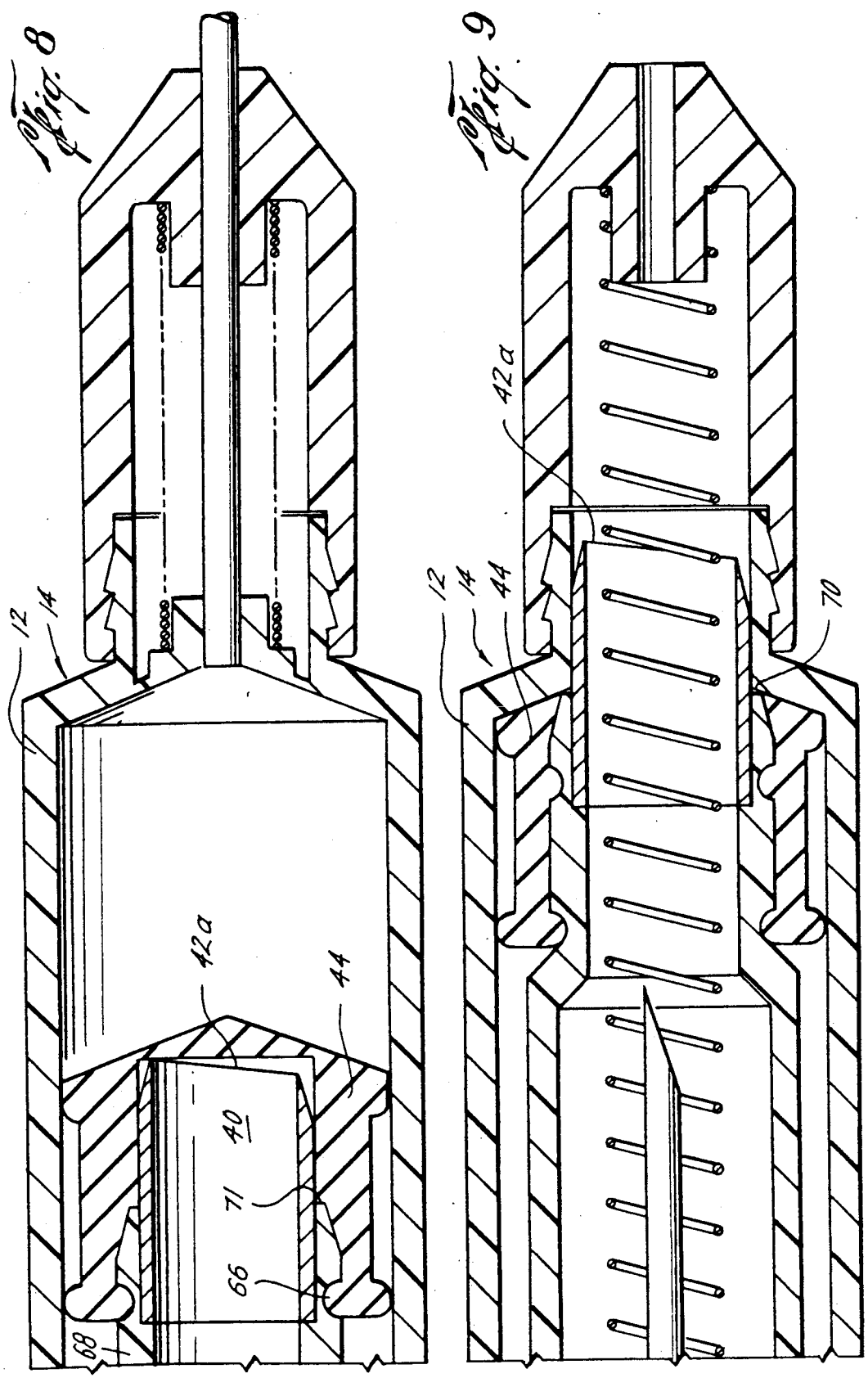

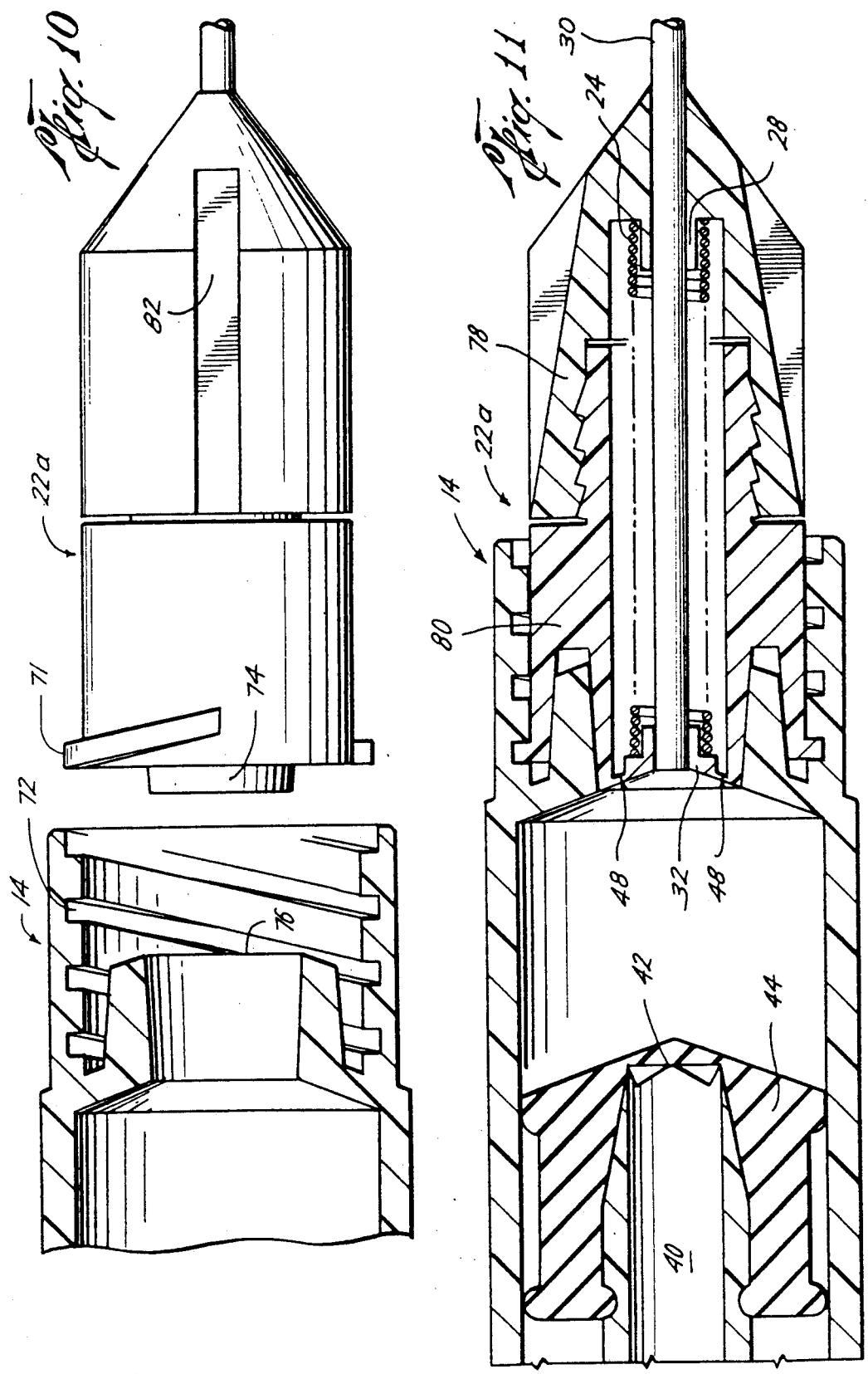

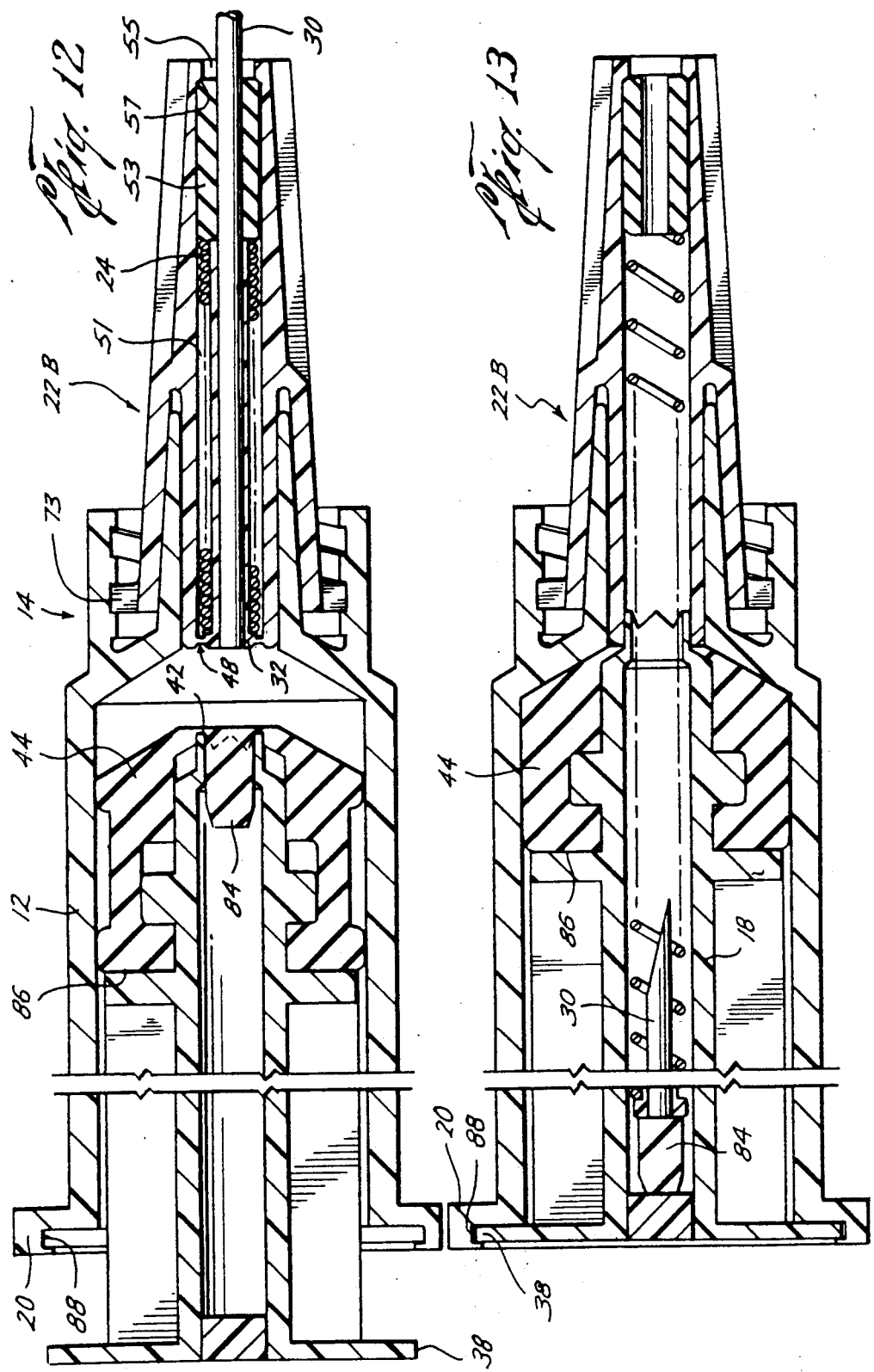

SAFETY SYRINGE WITH RETRACTABLE NEEDLE

BACKGROUND OF THE INVENTION

This invention relates to a safety syringe with retractable needle, and a method for delivering fluids to a patient and retracting the needle within the syringe after the fluid is delivered. In particular, the syringe device comprises a hollow plunger which is extendable into a cylindrical barrel thereby forcing fluid from the barrel and through a needle attached to one end of the barrel. The hollow plunger is capable of receiving the retractable needle once the plunger is fully extended into the barrel.

Hypodermic syringes are commonly used to deliver fluids from the syringe to one or more internal areas of the patient. Health care professionals which use hypodermic syringes often risk infection if they accidentally are scratched or punctured by the needle after injections are completed. Therefore, contaminated hypodermic needles present a substantial health hazard to anyone who handles or uses a hypodermic needle. Accordingly, there exists a need to protect personnel from accidental skin puncture injuries from such contaminated needles as well as the need to provide a safe and efficient means for disposing of the needles.

Recently there has been increased emphasis placed in designing hypodermic syringes with extendable shields which project over the needle area after injections are completed. Such devices often involve manual manipulation of the shield over the needle after the injection is completed. It follows that when the shield is manually extended over the needle, the operator's hand or fingers often come in contact with the tip of the needle, thus causing risk of contamination. In an effort to solve the problem of having to manually extend the shield, many devices have built-in biasing mechanism which automatically extend a shield over the needle after the injection is completed. These devices help reduce accidental contact with the needle, but they do not completely prevent access of the operator to the needle as would be the case if the needle were retracted inside the syringe. An extendable shield may still leave the needle accessible to finger tips through the unsealed forward end of the sheath. Further, the needle tip may become exposed if the sheath is moved or displaced by a jarring force.

In an effort to overcome the problems associated with extendable sheathings, many conventional devices protect the operator by manually retracting the needle inside the syringe. As the plunger is pushed toward the end of the barrel, it couples onto one end of the retractable needle and by manually pulling the plunger, the needle is drawn from its extended position into the syringe barrel. The conventional method of retracting a needle into the barrel by manually retracting the plunger has many disadvantages. First, the plunger must make secure connection with one of the needles, often involving detailed and complicated mechanisms. Second, the needle must be manually drawn into the syringe, thereby involving a two-handed operation. One hand is needed to secure the syringe, while the other is used to withdraw the plunger relative to the syringe. Third, the needle is typically retracted only after it is withdrawn from the patient.

Although manual retraction of a needle is preferred over needle-sheathing devices, their complicated structure and cumbersome nature may leave them undesirable for many applications. In an effort to overcome the difficulty in having to manually retract the needle, many conventional devices use a triggering mechanism which releases the needle from its extended position to a position inside the syringe. Typical triggering mechanisms involve activating arms or levers placed on the outside of the syringe. When these external levers are activated, the needle is automatically drawn into the syringe by one or more biasing mechanisms. While external levers having automatic retraction mechanisms provide an easier means for retracting the needle, they are often unduly complicated to both manufacture and operate. The trigger mechanisms are often configured at a point distant from the plunger, thereby requiring the operator to move his or her hand from a convenient point on the plunger to a distal trigger location. Further, they may be inadvertently activated if the triggering mechanism is accidentally activated.

Although many safety syringes are becoming easier to operate, they are becoming equally more difficult to manufacture. It is important that a safety syringe be both convenient to operate and economical to manufacture. Accordingly, syringes which allow convenient retraction of the needle must also be easy and inexpensive to manufacture. Conventional safety syringes appear unable to achieve both objectives.

SUMMARY OF THE INVENTION

The problems outlined above are in large part solved by the device and method of the present invention. That is, the safety syringe with retractable needle hereof provides convenient retraction of the needle inside the plunger by applying further pressure to the plunger after the plunger is fully extended into the barrel. There are no external levers or triggers either proximal or distal to the plunger tip and therefore the present invention does not suffer from the complicated nature of conventional devices. The safety syringe of the present invention is particularly useful for applying one-hand operation wherein a single forward motion upon the plunger causes fluid to be delivered and, after delivery, increased pressure on the plunger causes the needle to be automatically retracted. Thus, the present invention allows retraction of the needle either while the needle is imbedded or withdrawn from the patient. Furthermore, the present invention allows withdrawal or harvesting of fluid from a patient and after the fluid is withdrawn and delivered to a suitable container, the present invention can retract the needle to prevent reuse.

Broadly speaking, the present invention contemplates a syringe comprising a cylindrical barrel having first and second ends and fluid contained therebetween. A hollow plunger is inserted into the first end of the barrel and a hollow needle is attached to the second end of the barrel. A biasing means is attached to the second end of the barrel for biasing the needle and a portion of the second end of the barrel toward the hollow plunger. Further, means is provided for driving the fluid from the barrel and through the needle by applying forward pressure upon the plunger. Still further, means is provided for releasing the needle into the hollow plunger by applying additional forward pressure upon the plunger after the plunger is fully extended into the barrel. The biasing means includes a spring housing and a coil spring attached to the housing, wherein the coil spring is compressed between one end of the needle and the spring housing. The compressed coil spring provides biasing of the needle toward the hollow plunger. The releasing means comprises a sealing member attached to one end of the plunger and a cutting tip configured inside the sealing member, wherein the cutting tip is a cylindrical cutting means or knife extendable through the member, through the second end of the barrel and into a cavity within the spring housing.

The present invention also includes threads placed upon the spring housing for rotatable attachment onto the threaded distal end of the barrel. Alternatively, the spring housing may include a surface for permanent attachment by means such as sonic welding of the spring housing onto the distal end of the barrel. Still further, the spring housing may alternatively include at least one detent for snap-on fit with at least one detent on the distal end of the barrel. The above alternative configurations include, but are not limited to the many various configurations which may be used to attach the spring housing onto one end of the barrel or for biasing the needle toward the hollow plunger.

The present invention also includes a Luer-Lok arrangement wherein the spring housing is a self-contained unit. The Luer-Lok spring housing unit comprises a retainer connected to the distal end of the housing. The needle is configured to extend axially through the center of the housing from a connection point on the retainer to a point outside the housing. A compressed spring is axially displaced over the needle from a connection point on the retainer to a connection point substantially near the proximal end of the housing. Thus, the Luer-Lok arrangement provide a retainer within the spring housing as opposed to the threaded, sonic welded and snap-fit arrangements which do not include a retainer on the spring housing. The Luer-Lok embodiment advantageously allows the operator to quickly attach or detach an unused needle directly onto the syringe of the present device. The needle, contained within the Luer-Lok spring housing, is retractable by extending the plunger into the barrel such that when the plunger is fully extended, the cutting tip attached to the distal end of the plunger protrudes through the sealing member and retainer thereby releasing the compressed spring and forcing the needle into the hollow plunger.

The present invention also contemplates a method of delivering fluid to a patient through a needle of a hypodermic syringe and retracting the needle within the syringe after the fluid is delivered. In the method of fluid delivery, a device is provided having a needle which is implanted into the patient. Next, the operator applies one-handed force to one end of the plunger to force fluid from the barrel and into the patient. The plunger is then fully extended into the barrel to force all the fluid from the barrel. Next, by applying additional one-handed force to one end of the plunger, the cutting tip extends through the retainer thereby causing the biased needle to be released into the plunger. The inventors contemplate that the needle can be retracted into the plunger either while the needle is embedded into the patient or after the needle is withdrawn from the patient. In either case, delivery, as well as retraction, is achieved by a simple one-hand forward pressure upon the plunger.

The present invention therefore provides an improved device which allows convenient retraction of the needle by forward movement of the plunger and is also easy to manufacture and relatively inexpensive to produce. The triggering mechanism for retracting the needle is contained entirely within the syringe and thus does not suffer the disadvantages associated with conventional, external triggering devices. Furthermore, the present invention also contemplates means for retaining the plunger within the barrel after the needle is retracted within the plunger. Retention of the plunger and accompanying needle within the barrel prevents the contaminated needle from accidentally protruding out of the surrounding barrel. These and other advantages of the present invention will be further appreciated from the drawings and the detailed description provided below.

BRIEF DESCRIPTION OF THE DRAWINGS

FIG. 6 is an enlarged sectional view of a portion of the syringe, showing a cylindrical knife cutting tip attached to the distal end of a shortened section of the plunger;

FIG. 7 is an enlarged sectional view of a portion of the syringe of FIG. 6, showing the cylindrical knife being beveled at the tip of the shortened section;

FIG. 8 is an enlarged view partially in section of a portion of the syringe, showing the spring housing snap-fitted onto the syringe barrel;

FIG. 9 is an enlarged view partially in section of a portion of the syringe, showing penetration of the beveled cutting tip of FIG. 8 extending partially within the spring housing thereby releasing the needle into the plunger;

FIG. 10 is an enlarged view partially in section of a portion of the syringe, showing a Luer-Lok mating between the syringe barrel and the spring housing;

FIG. 11 is an enlarged view partially in section of a portion of the present syringe, showing the spring housing mated with the syringe barrel by Luer-Lok means found in FIG. 10;

FIG. 12 is an enlarged view partially in section of a locking plunger portion and a portion of the present syringe, showing an alternative form of the spring housing mated with the syringe barrel by Luer-Lok means; and, FIG. 13 is an enlarged view partially in section of a locking plunger portion and a portion of the present syringe of FIG. 12, showing the cutting tip fully extended through the retainer thereby releasing the needle into the hollow plunger.

DETAILED DESCRIPTION OF THE PREFERRED EMBODIMENTS

Figure 1:
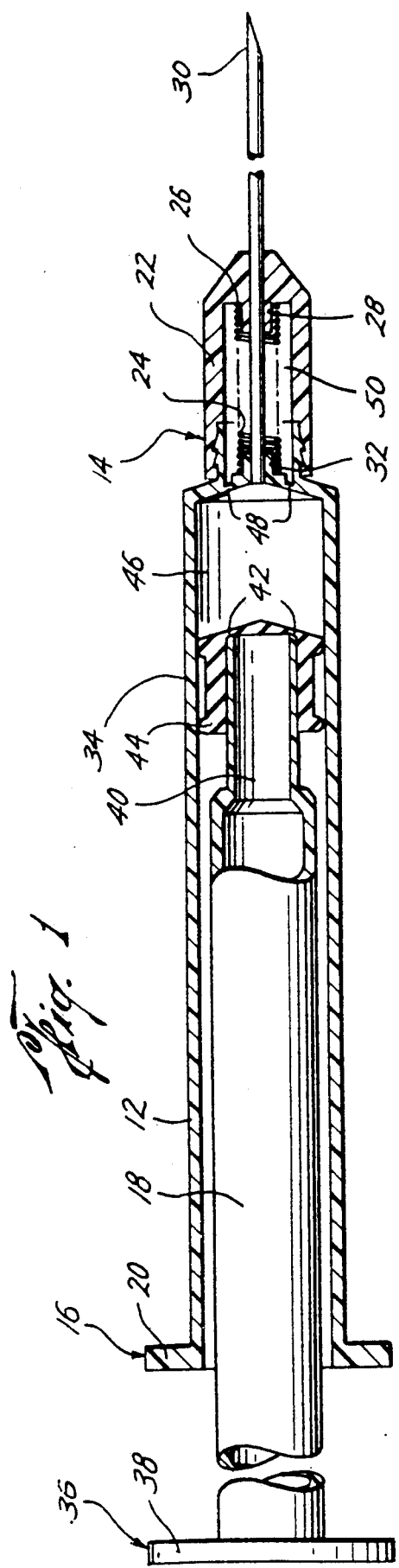
FIG. 1 is an elevation view partially in section of a syringe constructed according to the present invention.

Referring to the drawings, FIG. 1 illustrates safety syringe 10 including cylindrical barrel 12 having a distal end 14 and proximal end 16. Proximal end 16 is generally open thereby allowing a plunger 18 to be inserted within barrel 12. Proximal end 16 may include a flange 20 upon which the operator's fingers may be secured when actuating plunger 18.

The barrel's distal end 14 is configured to receive a spring housing 22. Housing 22 functions to contain one end of a spring 24 which becomes compressed against distal end 14 when housing 22 is attached to end 14. Spring distal end 26 is securely held upon flange 28 of spring housing 22. As housing 22 is attached to distal end 14, spring 24 slides over needle 30 and is compressed around 30 between housing flange 28 and a portion of the distal end 14, or retainer 32. Thus, spring housing 22 functions to provide a biasing force against retainer 32 when housing 22 is attached to barrel 12. Compression force on spring 24 causes retainer 32 and attached needle 30 to be biased toward plunger 18.

Plunger 18 is a hollow cylindrical member having a distal end 34 and a proximal end 36. Proximal end 36 is closed and, may contain a plunger flange 38 to provide a convenient pressure point to accommodate an operator's finger. Configured at plunger distal end 34 is a shortened cylindrical section 40. Section 40 is hollow having an inner diameter less than the inner diameter of plunger 18. Also, the outer diameter of section 40 is preferably less than the outer diameter of plunger 18. At the distal end of section 40, between the outer diameter and inner diameter of section 40, is a cutting tip 42 generally configured as a cylindrical knife.

Surrounding tip 42 and a portion of section 40 is a sealing member 44. Sealing member 44 is made of a penetrable soft, flexible rubber-like material or plastic material having at least one radially extending protrusion having an outer diameter which sliding engages with the inner diameter of barrel 12. Member 44, while allowing sliding engagement, substantially prevents fluid leaking from the distal side to the proximal side of member 44. Thus, member 44 provides a substantially fluid-type sealing engagement with the inner diameter of barrel 12 such that fluid in chamber 46 is forced through needle 30 by forward movement of plunger 18. Member 44 is preferably made of a rubber or elastomer material, but can be of any material which provides substantial fluid-type sliding engagement with the inner diameter of barrel 12. Further, barrel 12 is of any material which has a substantially smooth inner diameter and therefore may include, but is not limited to plastic, glass, etc.

Figure 2:
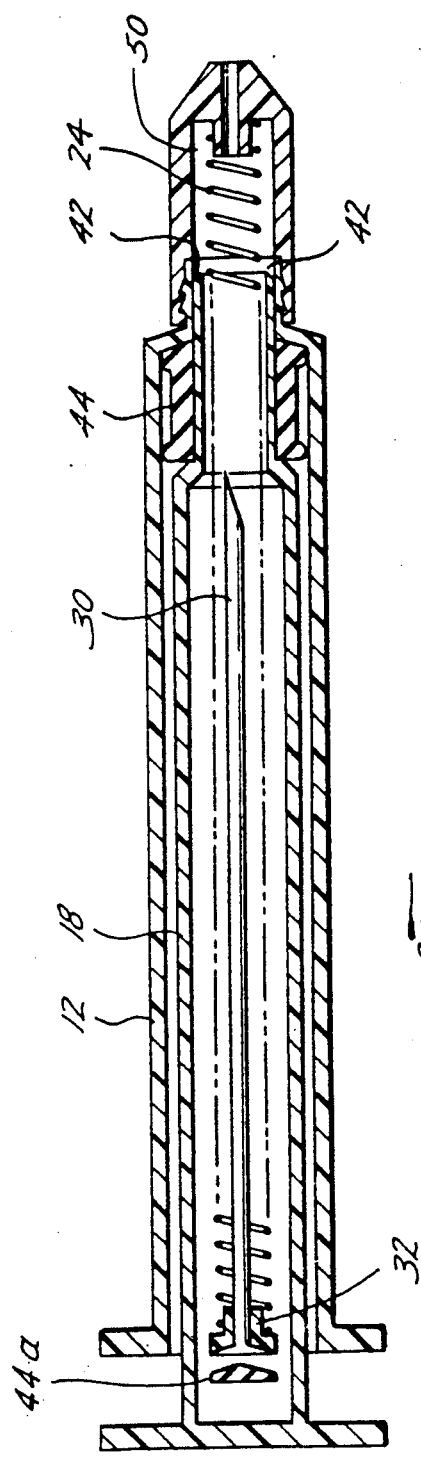
FIG. 2 is an elevation view partially in section of the syringe constructed according to the present invention, showing the plunger fully extended into the syringe and the needle retracted inside the plunger.

FIG. 2 illustrates the functionality of the retractable needle syringe of the present invention. As plunger distal end 34 is moved from barrel proximal end 16 to barrel distal end 14, fluid is forced from chamber 46 through needle 30. After all the fluid is withdrawn from syringe 10, and the distal end of member 44 is flush with barrel distal end 14, additional force on plunger proximal end 36 causes cutting tip 42 to penetrate through sealing member 44 and retainer 32. Once retainer 32 is severed from barrel distal end 14 by cutting tip 42, compressed spring 24 forces retainer 32 and attached needle 30 into hollow plunger 18. A portion of the soft sealing member 44 which is cut by cutting tip 42 and displaced by spring 24 is shown in FIG. 2 as 44A. Portion 44A is forced into plunger 18 by the releasing force of spring 24. The cylindrical knife of tip 42 also cuts through a thin tab or web member 48 thereby releasing retainer 32 and attached needle 30 into plunger 18. Tab 48 is constructed of any material which is easily penetrable by tip 42 but remains rigid until penetration. Tab 48 thereby may be constructed of plastic, thin metal, thread or the like. It is understood, however, that tab 48 is not limited to any particular construction as long as the construction chosen performs the desired function as outlined herein.

As shown in FIG. 2 and herein below, shortened section 40 is cylindrical and tip 42 is substantially circular, both having radial dimensions which are substantially equal to and accommodated by cavity 50. Cavity 50 is preferably a partially cylindrical shaped bore which extends axially along spring housing 22. Cavity 50 also accommodates spring 24 between spring housing flange 28 and retainer 32. As cutting tip 42 and cylindrical section 40 are forced through member 44 and tab 48 and into cavity 50, the force of coil spring 24 causes portion 44A and retainer 32 to travel smoothly through the hollow section 40. The initial force of compressed spring 24 easily moves portion 44A and retainer 32 within the smaller diameter section 40. As spring 24 becomes extended and the biasing force is correspondingly reduced, the larger inner diameter hollow plunger easily accommodates the retracted components. Thus, it is important to note that shortened section 40 is long enough to align with and penetrate into cavity 50 but is not too long to cause the retracted components to bind or become plugged inside section 40. Any length which is appropriate for both purposes thereby falls with the scope and spirit of this invention.

Figure 3:
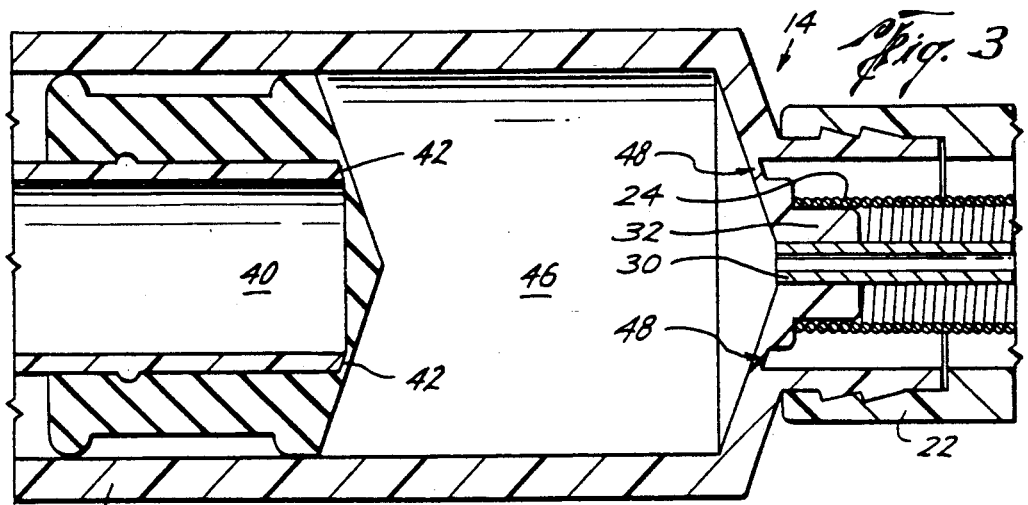
FIG. 3 is an enlarged sectional view of a portion of the syringe where the barrel interfaces with the spring housing.
Figure 4:
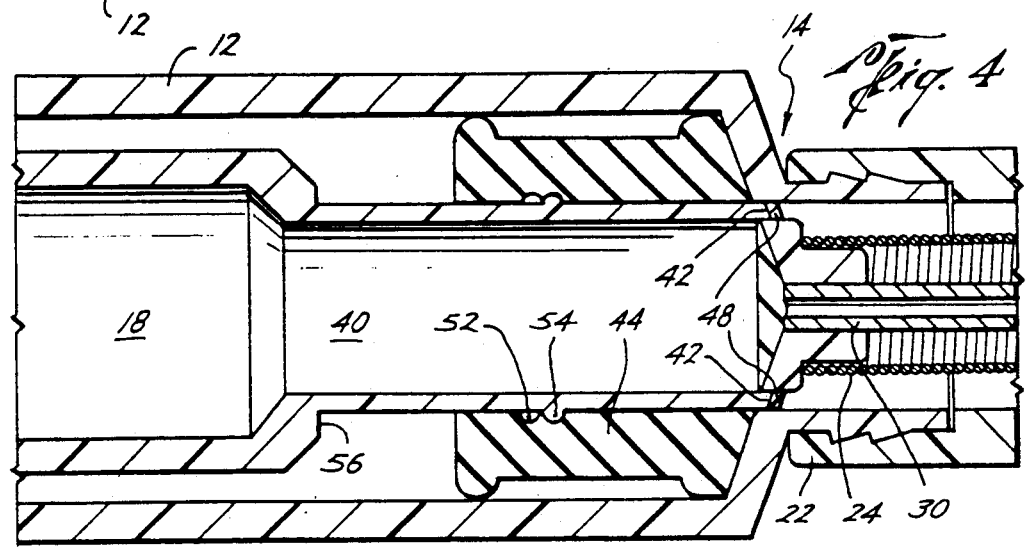
FIG. 4 is an enlarged sectional view of a portion of the syringe of FIG. 3, showing the plunger fully extended into the barrel and the cutting tip extending through the sealing member and dislodging a portion of the retainer.
Figure 5:
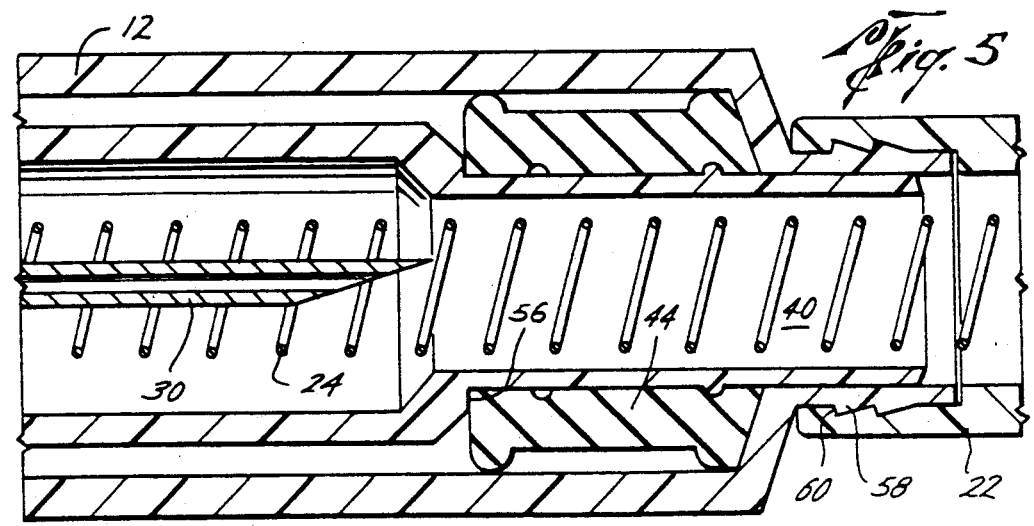
FIG. 5 is an enlarged sectional view of a portion of the syringe of FIGS. 3 and 4, showing the cutting tip fully extended through the retainer thereby releasing the needle into the hollow plunger.

FIGS. 3–5 illustrate, in an enlarged view, the release mechanism of the present invention. Shown in FIG. 3 is sealing member 44 not yet fully engaged with barrel distal end 14. Tabs 48 and cutting tip 42 are shown axially aligned with one another. Spring 24 is compressed against retainer 32 to provide biasing force of attached needle 30 through hollow cylindrical section 40.

FIG. 4 illustrates plunger 18 being forced further into barrel 12 such that sealing member 44 abuts against barrel distal end 14. Accordingly, all the fluid is forced from chamber 46 through hollow needle 30 thereby evacuating all fluid from the syringe. As member 44 is extended fully into barrel 12, female detents 52 on the inner diameter of member 44 release male detents 54 on the outer diameter of section 40 so that section 40 can extend within cavity 50 while member 44 remains in barrel 12.

Female and male detents 52 and 54, respectively, function to maintain member 44 configure about the distal end of section 40. As the distal end of section 40 or cutting tip 42 traverses member 44 and tab 48 the mating of female and male detents 52 and 54 is broken as shown in FIGS. 4 and 5. Once cutting tip 42 extends into cavity 50, female and male detents 52 and 54 separate thereby allowing member 44 to remain stationary within barrel 12 and secures against distal end 14. Further, member 44 also provides a stop means, wherein edge 56 of plunger 18 comes to rest against member 44 when section 40 is fully extended in cavity 50. Edge 56 provides palpable indicia of the fullest extent upon which plunger 18 can be extended. FIG. 5 illustrates this point. When the operator applies pressure to plunger proximal end 36 via flange 38, he or she extends member 44 against barrel distal end 14 to forcibly drive fluid from chamber 46 and into needle 30. The operator can further press upon flange 38, thereby causing further extension of cutting tip 42 through member 44 and tab 48. Full extension of plunger is achieved when the operator palpably detects edge 56 against member 44. The stop means provided by edge 56 will ensure that cutting tip 42 does not extend beyond the distal end of spring housing 22. Furthermore, edge 56 is configured in such a way as to give section 40 sufficient axial length to allow the retractable components to extend through section 40 without becoming jammed or bound therein.

FIGS. 3-6 illustrate one embodiment of cutting tip 42, wherein the tip comprises a cylindrical knife edge for piercing member 44 and tab 48 simultaneously around the entire circumference of the knife edge. In many instances, it is desirable to have a beveled cutting tip 42A, shown in FIGS. 7-9, to pierce one portion of member 44 and tab 48 prior to other portions. A beveled tip 42A may allow for easier piercing and penetration of member 44 and tab 48. It is important to note, however, that either embodiment shown in FIG. 6 or FIG. 7 for cutting tip 42 can be used, or other embodiments can be used, as long as the basic function remains, namely that member 44 and tab 48 are cut cleanly and easily leaving a smooth outer surface for easy deployment through the inner diameter surface of section 40 and plunger 18.

FIGS. 4, 6 and 7 also show various embodiments for attaching spring housing 22 to barrel distal end 14. FIGS. 1-5 illustrate a snap fit configuration between housing 22 and barrel distal end 14. At least one bump, protrusion, tab or detent 58 is arranged on the outer surface of barrel distal end 14. Bump 58 is arranged to receive a cavity or recess 60 within housing 22 when housing 22 is axially displaced over and onto distal end 14. The mating of recess 60 and bump 58 provides secure attachment means between housing 22 and distal end 14. Further, snap-fit arrangement of FIGS. 1-5 allows quick axial compression of spring 24 about needle 30.

Although snap-on attachment is convenient, many other methods of attaching housing 22 to barrel distal end 14 are also possible. Specifically, a threaded mating means might be preferred in certain applications such as, for example, military, industrial, veterinarian or self-administering applications. Threads 62 placed on distal end 14 can be used to mate with threads placed on the proximal end of housing 22. Threaded mating occurs by first placing the spring attached to housing 22 over needle 30 attached to distal end 14. Second, housing 22 is rotatably inserted onto distal end 14 via mating threads therebetween. As housing 22 is brought in closer contact to distal end 14, spring 24 is compressed thereby providing biasing force against retainer 32 and attached needle 30 toward plunger 18.

FIG. 7 illustrates another embodiment for attaching housing 22 to barrel distal end 14. Housing 22 can be securely fixed to distal end 14 by sonically welding abutting radial surface 64. Housing 22 is axially slid over distal end 14 causing spring 24 to become compressed against retainer 32. Once housing 22 is in place, sonic welds are applied to securely affix abutting surfaces 64 between housing 22 and distal end 14. Also shown in FIG. 7 are small recesses 49 which define a thinner dimension in tab 48 so as to ensure easy and predictable tear or cutting of tab 48 by cutting tip 42 or beveled cutting tip 42a.

It is important to note that FIGS. 6-8 illustrate various means by which sealing member 44 are, or are not, coupled to section 40. Member 44 of FIG. 6 can be simply placed over the distal end of section 40 and not secured thereto. Or, member 44 may be glued to section 40 such that the intrigity of the glue is broken when section 40 extends partially within cavity 50. FIG. 7 illustrates that the section 40 and member 44 are coupled by female and male detents 52 and 54 described above. Still further, FIG. 8 illustrates member 44 being secured to section 40 via a catch mechanism or detents 66 distal from section 40. Catch 66 is arranged between member 44 and a radially extending section 68.

FIG. 9 illustrates the securing embodiment of FIG. 8 when plunger 18 is fully driven into barrel 12. As beveled cutting tip 42A extends through member 44 and tab 48, catch 66 releases member 44 from its secured position on section 40. Accordingly, member 44 is driven from the distal end of section 40 toward the proximal end as plunger 18 is fully driven into barrel 12. Plunger 18 is extended into barrel 12 until radially extending lip 70 comes to rest against the inner surface of barrel distal end 14. Although FIGS. 3-9 show many embodiments for axially displacing member 44 on section 40, it is important to note that there are numerous other types of configurations which can be achieved without departing from the scope and spirit of this invention. Any form of attachment which provides axial displacement of member 44 is envisioned by the inventors and accordingly, fall within the present invention's scope. Also, any form of embodiment which allows palpable feedback to the operator of when tip 42 is fully extended is also included in this application. The embodiments shown in FIGS. 3-9 serve only as examples of many different ways of achieving the same function with one example differing only in terms of ease of manufacture from that of another.

FIGS. 10 and 11 show another embodiment by which a self-contained spring housing 22A is secured via a Luer-Lok arrangement with barrel distal end 14. Instead of having needle 30 and retainer 32 secured via tabs 48 to distal end 14, the lure-lock arrangement allows spring housing 22A to contain needle 30 and retainer 32. Spring housing 22A is rotatably attached to distal end 14 by engaging male threads 71 within female threads 72. As housing 22A is drawn against distal end 14, the outer diameter of cylindrical opening 74 sealingly abuts against the inner diameter of opening 76.

As shown in FIG. 11, spring housing 22A includes a forward and aft section 78 and 80, respectively. Aft section 80 comprises needle 30 and retainer 32 attached to one end and forward section 78 attached to the other end. Forward section 78 comprises spring 24 attached to spring housing flange 28. When forward section 78 is attached to aft section 80, spring 24 is displaced over needle 30 and compressed against retainer 32 to provide biasing force of retainer 32 toward plunger 18. As is indicated hereinabove, forward section 78 can be attached to aft section 80 by any of the various means used herein, including, but not limited to, snap-on, sonic weld, threads, etc. If threaded attachment means are used, a slit or groove 82 can be placed on the outer surface of forward section 78 to facilitate screw-on movement of forward section 78 onto aft section 80. Still further, cutting tip 42, sealing member 44 and section 40 can be configured in any way which allows penetration through member 44 and tab 48 while allowing member 44 to become axially displaced along section 40.

Illustrated in FIG. 12 is another embodiment showing Luer-Lok mating of syringe barrel 12 to a spring housing 22B. Spring housing 22B, unlike spring housing 22A, is designed having a bore 51 extending from the distal end of spring housing 22B to retainer 32. Place over needle 30 and within bore 51 is spring 24. In order to compress spring 24 against retainer 32, plug 53 is dimensioned to engage between the walls of bore 51 and outer surface of needle 30. Plug 53 is preferably a rigid member comprising a plastic material which can traverse opening 55 to snap-fit reside in its illustrated position. Plug 53 is of sufficient strength to retain compressive force of spring 24 when fully inserted in its snap-fit position. Plug 53 allows spring housing 22B to be configured onto barrel 12 which is of a size and shape that can be made standard in the industry. Applicant postulates other ways to retain spring 24 by such means as a cotter pin, etc., however, other such means fall within the spirit of this invention. Configured at the proximal end of spring housing 22B is a flange or a set of at least two protrusions 73 which can be rotatably received in distal end 14 similar to a standard Luer-Lok mating scheme.

Shown in FIG. 12 is a guiding member 84 contained within cutting tip 42. Member 84 is a unitary part of member 44 and functions to maintain correct alignment of cutting tip 42 in relation to the inner diameter of barrel 12 so that cutting tip 42 is in relatively precise alignment with tab 48 as tip 42 is pushed down barrel 12. Also shown in FIG. 12 is an edge 86 which pushes against a portion of member 44 as plunger 18 is extended into barrel 12. When cutting tip traverses tab 48 and protrudes into bore 51, edge 86 causes member 44 to axially compress and radially expand. Spring 24, compressed between plug 53 and retainer 32, is released as shown in FIG. 13 thereby forcing needle 30 into hollow plunger 18. In order to retain plunger 18 in the fully extended position within barrel 12, a retaining recess 88 may be configured on barrel flange 20 to retain radially extending flange 38 when plunger 18 is fully extended. As shown in FIG. 13, when plunger 18 is fully extended, flange 38 causes flange 20 to radially flex outward thus accommodating flange 38 within recess 88. Further, member 84 is dimensioned to easily slide within plunger 18 cavity without becoming constricted therein once plunger 18 is fully extended and needle 30 is retracted.

FIGS. 10-13 illustrate the numerous possibilities available in designing and manufacturing an uncomplicated and relatively inexpensive syringe of the present invention. Cutting tip 42, the interface between member 44 and section 40, the attachment of forward and aft sections 78 and 80 all allow manufacturing flexibility to achieve a specific purpose or outcome. A LuerLok self-contained spring housing 22a or 22b is preferred in many medical applications and is advantageous when using syringes of varying capacities with standard needles. Conversely, needles of various lengths or gauges can be also attached to barrels of varying capacities. Therefore, Luer-Lok arrangements have become very popular in recent years. Accordingly, FIGS. 10-13 take advantage of the Luer-Lok convenience in adapting the Luer-Lok system to the present invention. Regardless of which embodiment is used, either Luer-Lok, screw-on, snap-on or permanent attachment, the present invention provides an improved safety syringe with a triggering mechanism internal to the syringe for allowing automatic retraction of the needle into the plunger by a simple and continuous forward motion of the plunger into the barrel. Palpable indicia is provided internal to the syringe for signalling when member 44 abuts against the distal end 14 and additional palpable indicia is provided for signalling when cutting tip 42 is fully extended into cavity 50.

The safety syringe with retractable needle of the present invention is therefore capable of delivering fluid to a patient and subsequently retracting the needle within the syringe after the fluid is delivered. By implanting needle 30 into the patient and applying one-handed force to plunger flange 38 by squeezing plunger flange 38 toward barrel flange 20, fluid is forced from chamber 46 through needle 30 and into the patient. Abutment of member 44 against distal end 14 signals to the operator that all the fluid has been delivered. By applying additional one-handed force to plunger flange 38, the operator will send cutting tip 42 through member 44 and tab 48 thereby causing the biasing force of spring 24 to release needle 30, retainer 32 and portion 44A into plunger 18. The operator can choose to either retract needle 30 while the needle is embedded in the patient or can retract needle 30 after he or she withdraws needle 30 from the patient. Either procedure is acceptable. Further, once needle 30 is retracted into plunger 18, syringe 10 can no longer be used and is permanently destroyed. A non-reusable syringe 10 of the present invention provides the advantage of not allowing reoccurring use of a contaminated needle.

The foregoing description of the present invention has been directed to particular preferred embodiments. It will be apparent, however, to those skilled in the art that modifications and changes in both apparatus and method may be made without departing from the scope and spirit of the invention. For example, cutting tip 42 can be configured in any fashion beyond a cylindrical knife or beveled knife described herein as long as the desired function is obtained. Further, member 44 can be axially displaced on section 40 using means other than glue, detents or, as pointed out above, can be simply placed over tip 42 and not secured whatsoever. Still further, tab 48 can be described in any format which allows retention of compressed spring 24 but can be rapidly and easily penetrated by cutting tip 42. Still further, spring housing 22 can be secured to distal end 14 by any means which provides compression of spring 24 while preventing substantial movement of needle 33. Still further, Luer-Lok arrangement can be of a self-contained unitary body or, as shown in FIGS. 10 and 11, have separable forward and aft sections for accessing spring 24. It is certainly possible that spring housing 22A can be manufactured as a unitary body with needle 30, spring 24 and retainer 48 contained and sealed therein. Therefore, it is the applicant's intention in the following claims to cover all such equivalent modifications and variations which fall within the true spirit and scope of this invention.

What is claimed is:

1. A syringe, comprising:
   a cylindrical barrel having first and second ends and fluid contained therebetween;
   a hollow plunger inserted into the first end of said barrel;
   a hollow needle attached to the second end of said barrel;
   biasing means attached to the second end of said barrel for biasing said needle toward said hollow plunger;
   means for driving said fluid from said barrel and through said needle by applying forward pressure upon said plunger;

a sealing member attached to one end of said plunger for sliding engagement with the inside diameter of said barrel; and a cutting tip configured inside said sealing member for cutting through said member and the second end of said barrel such that said biasing means releases said needle into the said plunger when said plunger is fully extended into said barrel.

2. The syringe as recited in claim 1, wherein said cutting tip is a beveled knife extendable through said member, through the second end of said barrel and into the cavity within said spring housing.

3. The syringe as recited in claim 1, further comprising means for retaining said plunger within said barrel after said needle is released into said plunger.

4. A non-reusable syringe having a retractable needle, comprising:
a cylindrical barrel having a proximal end and a distal end, said proximal end is open and said distal end is adapted to receive said needle;
a hollow cylindrical plunger having a proximal end and a distal end, said distal end is inserted into the proximal end of said barrel;
a sealing member adjacent a cutting tip attached to the distal end of said plunger;
retainer means connected between said needle and the distal end of said barrel for retaining said needle in a biased position extending outside said barrel; and,
means for extending said sealing member against the distal end of said barrel and further extending said cutting tip through said sealing member and said retainer thereby releasing said needle from said biased position and into said hollow plunger.

5. The syringe as recited in claim 4, wherein the distal end of said barrel further comprises threads for rotatably receiving a spring housing containing a spring axially displaceable over said needle, said spring is compressed against said retainer means by screwing said housing onto the distal end of said barrel.

6. The syringe as recited in claim 4, wherein the distal end of said barrel further comprises a surface to which a spring housing containing a spring is sonically welded, said spring is axially displaceable over said needle and compressed against said retainer means when said spring housing is sonically attached onto the distal end of said barrel.

7. The syringe as recited in claim 4, wherein the distal end of said barrel further comprises at least one primary detent on the outer diameter of said barrel for receiving a spring housing containing at least one secondary detent on the inner diameter of said housing which snap fits over the male detent, said housing comprising a spring axially displaceable over said needle such that said spring is compressed against said retainer means when said spring housing is snap fitted onto the distal end of said barrel.

8. The syringe as recited in claim 4, wherein the sealing member is a soft rubber-like material capable of movement within said barrel while maintaining sealing engagement with the inner diameter of said barrel.

9. The syringe as recited in claim 4, further comprising a spring housing having a cavity for receiving a cylindrical shortened section of the distal end of said plunger having lesser inner diameter than said plunger.

10. The syringe as recited in claim 9, wherein said extending means forces said cutting tip through said sealing member and said retainer means and into said cavity thereby freeing said needle and a portion of said retainer to travel through said shortened section and reside within said hollow plunger.

11. The syringe as recited in claim 9, wherein said cutting tip is a cylindrical knife attached to the distal tip of said shortened section, said cylindrical knife and said cylindrical shortened section are of sufficient diameter to travel substantially within said cavity when said extending means is fully actuated.

12. The syringe as recited in claim 9, wherein said cutting tip is a beveled cylindrical knife attached to the distal tip of said shortened section, said beveled cylindrical knife and said cylindrical shortened section are of sufficient diameter to travel substantially within said cavity when said extending means is fully actuated.

13. The syringe as recited in claim 4, further comprising:
a flange connected to the proximal end of said plunger; and,
means connected to the proximal end of said barrel for retaining said flange when said plunger is fully extended into said barrel.

14. A syringe, comprising:
a cylindrical barrel having a proximal end and a distal end;
a hollow cylindrical plunger having a proximal end and a distal end, said distal end is inserted into the proximal end of said barrel;
a spring housing having a proximal end and a distal end, said housing further comprising:
a retainer connected to the proximal end of said housing;
a needle extending axially through the center of said housing from a connection point on said retainer to a point outside said housing;
a compressed spring axially displaced over said needle from a point on said retainer to a connection point substantially near the distal end of said housing; and,
means for releasably securing the proximal end of said housing to the distal end of said barrel.

15. The syringe as recited in claim 14, further comprising:
a sealing member surrounding a cutting tip attached to the distal end of said plunger; and,
means for extending said plunger into said barrel in axial alignment with said retainer such that when said plunger is fully extended, said cutting tip protrudes through said sealing member and said retainer thereby releasing said needle into said hollow plunger.

16. The syringe as recited in claim 14, wherein said releasably securing means comprises a Luer-Lok having one mating part secured to the distal end of said barrel and the other mating part secured to the proximal end of said housing.

17. The syringe as recited in claim 14, wherein the distal end of said barrel comprising threads for rotatably receiving mating threads on the proximal end of said spring housing.

18. The syringe as recited in claim 14, wherein the distal end of said barrel comprising threads for rotatably receiving a flange on the proximal end of said spring housing.

19. The syringe as recited in claim 14, wherein said spring housing further comprises:

a first member having a bore extending from the distal end of said first member to said retainer at the proximal end of said first member;

a second member having a bore extending from the proximal end of said second member to a point substantially near the distal end of said second member;

means for coupling said first and second members to define a mutual cavity containing said compressed spring; and, means for releasably securing said first and second members to the distal end of said barrel.

20. The syringe as recited in claim 19, wherein said releasably securing means comprises a Luer-Lok having one mating part secured to the distal end of said barrel and the other mating part secured to the proximal end of said first member.

21. The syringe as recited in claim 14, wherein said spring housing further comprises:

a third member having a bore extending from the distal end of said third member to said retainer at the proximal end of said third member;

said spring placed axially over said needle and within said bore with the proximal end of said spring abutting against said retainer; and, plug means placed over said needle and into the proximal end of said third member for compressing said spring against said retainer.

22. The syringe as recited in claim 21, wherein said silastic plug means comprises a rigid material.

23. A non-reusable syringe having a retractable needle, comprising:

a cylindrical barrel having a proximal end and a distal end, said proximal end is open and said distal end is adapted to receive said needle;

a hollow cylindrical plunger having a proximal end and a distal end, said distal end is inserted into the proximal end of said barrel;

a rubber-like sealing member placed over the distal end of said plunger and secured by mating detents on both said sealing member and said plunger;

a cutting tip comprising a cylindrical knife attached to the proximal end of said plunger and contained within said sealing member;

a retainer connected to the distal end of said barrel for retaining said needle to the distal end of said barrel;

a spring housing attachable to the distal end of said barrel, comprising:

a coil spring that is compressible over said needle and between said housing and said retainer when said housing is attached to said barrel;

a cavity radially surrounding said spring and in close proximity to said retainer when said housing is attached to said barrel; and, means for extending said plunger into said barrel and, when said plunger is fully extended into said barrel, to further extend said cutting tip through said sealing member and said retainer and into said cavity thereby releasing said compressed spring and said attached needle into said hollow plunger.

24. The syringe as recited in claim 23, wherein said spring housing comprising threads for rotatable attachment onto threaded distal end of said barrel.

25. The syringe as recited in claim 23, wherein said spring housing having a surface for permanent attachment onto the distal end of said barrel.

26. The syringe as recited in claim 23, wherein said spring housing having at least one detent for snap-on fit with at least one detent on the distal end of said barrel.

27. The syringe as recited in claim 23, wherein said cylindrical knife is beveled with one portion of said cutting tip being longer than another portion.

28. A method of delivering fluid to a patient through a needle of a hypodermic syringe and retracting the needle within the syringe after the fluid is delivered, comprising the steps of:

providing a device comprising an elongated tubular barrel for containing fluid, a plunger having a cutting tip insertable into one end of said barrel and a retainer attached to the opposite end of said barrel for retaining said needle in a biased position outside said barrel;

implanting the needle of said device in said patient;

applying one-handed force to one end of said plunger for coercing fluid from said barrel and into said patient;

extending said plunger fully into said barrel; and, applying additional one-handed force to one end of said plunger so that said cutting tip extends through said retainer and thereby releases said biased needle into said plunger.

29. The method as recited in claim 28, further comprising withdrawing said needle from said patient prior to applying additional force step.

30. The method as recited in claim 28, further comprising maintaining said needle implanted in said patient prior to applying additional force step.

31. The method as recited in claim 28, wherein said providing step comprises attaching one end of a coil spring to said retainer and said needle for biasing said needle toward said plunger.

* * * * *